(12) United States Patent
Gross et al.

(10) Patent No.: US 7,387,603 B2
(45) Date of Patent: *Jun. 17, 2008

(54) INCONTINENCE TREATMENT DEVICE

(75) Inventors: Yossi Gross, Moshav Mazor (IL); Ehud Cohen, Ganei Tikva (IL); Israel Nissenkorn, Tel Aviv (IL); David Lifschitz, Zurich (IL)

(73) Assignee: AMS Research Corporation, Minnetonka, MN (US)

(*) Notice: Subject to any disclaimer, the term of this patent is extended or adjusted under 35 U.S.C. 154(b) by 26 days.

This patent is subject to a terminal disclaimer.

(21) Appl. No.: 10/999,824

(22) Filed: Nov. 30, 2004

(65) Prior Publication Data

US 2005/0113881 A1 May 26, 2005

Related U.S. Application Data

(63) Continuation of application No. 10/047,135, filed on Jan. 15, 2002, now Pat. No. 6,896,651, which is a continuation of application No. 09/413,272, filed on Oct. 6, 1999, now Pat. No. 6,354,991, which is a continuation-in-part of application No. 09/167,244, filed on Oct. 6, 1998, now abandoned.

(30) Foreign Application Priority Data

Dec. 9, 1998 (IL) .................................... 127481

(51) Int. Cl.
*A61F 2/02* (2006.01)

(52) U.S. Cl. ...................................... 600/30

(58) Field of Classification Search ................. 600/29, 600/30; 607/2, 39, 40, 48, 115, 116, 138
See application file for complete search history.

(56) References Cited

U.S. PATENT DOCUMENTS

| 3,628,538 | A | * | 12/1971 | Vincent et al. | ............... 607/62 |
| 3,640,284 | A | * | 2/1972 | De Langis | .................... 607/71 |
| 3,662,758 | A | | 5/1972 | Glover | |
| 3,866,613 | A | | 2/1975 | Kenny et al. | |
| 3,870,051 | A | | 3/1975 | Brindley | |
| 3,926,178 | A | | 12/1975 | Feldzamen | |
| 3,941,136 | A | | 3/1976 | Bucalo | |
| 3,983,865 | A | | 10/1976 | Shepard | |

(Continued)

FOREIGN PATENT DOCUMENTS

WO     WO 00/01320     1/2000

OTHER PUBLICATIONS

U.S. Appl. No. 60/091,762, filed Jul. 06, 1998, Loeb et al.

(Continued)

*Primary Examiner*—Samuel G Gilbert
(74) *Attorney, Agent, or Firm*—Jose' W. Jimenez; Kimberly K. Baxter; Gregory L. Koeller

(57) ABSTRACT

A device and method for treatment of urinary stress incontinence. At least one electrode is implanted in a pelvic muscle of a patient. A control unit receives signals indicative of abdominal stress in the patient and responsive thereto applies an electrical waveform to the electrode which stimulates the muscle to contract, so as to inhibit involuntary urine flow through the patient's urethra due to the stress.

35 Claims, 6 Drawing Sheets

U.S. PATENT DOCUMENTS

| | | | | |
|---|---|---|---|---|
| 3,983,881 | A | 10/1976 | Wickham | |
| 4,023,574 | A | 5/1977 | Nemec | |
| 4,106,511 | A | 8/1978 | Erlandsson | |
| 4,136,684 | A | 1/1979 | Scattergood et al. | |
| 4,139,006 | A | 2/1979 | Corey | |
| 4,153,059 | A | 5/1979 | Fravel et al. | |
| 4,157,087 | A | 6/1979 | Miller et al. | |
| 4,165,750 | A | 8/1979 | Aleev et al. | |
| 4,177,819 | A | 12/1979 | Kofsky et al. | |
| 4,222,377 | A | 9/1980 | Burton | |
| 4,290,420 | A | 9/1981 | Manetta | |
| 4,406,288 | A | 9/1983 | Horwinski et al. | |
| 4,457,299 | A | 7/1984 | Cornwell | |
| 4,492,233 | A | 1/1985 | Petrofsky et al. | |
| 4,515,167 | A | 5/1985 | Hochman | |
| 4,542,753 | A | 9/1985 | Brenman et al. | |
| 4,568,339 | A | 2/1986 | Steer | |
| 4,571,749 | A | 2/1986 | Fischell | |
| 4,580,578 | A | 4/1986 | Barsom | |
| 4,688,575 | A | 8/1987 | DuVall | |
| 4,731,083 | A | 3/1988 | Fischell | |
| 4,735,205 | A * | 4/1988 | Chachques et al. | 607/2 |
| 4,739,764 | A | 4/1988 | Lue et al. | |
| 4,785,828 | A | 11/1988 | Maurer | |
| 4,881,526 | A | 11/1989 | Johnson et al. | |
| 5,013,292 | A | 5/1991 | Lemay | |
| 5,103,835 | A | 4/1992 | Yamada et al. | |
| 5,285,781 | A | 2/1994 | Brodard | |
| 5,291,902 | A * | 3/1994 | Carman | 607/138 |
| 5,324,323 | A * | 6/1994 | Bui | 607/119 |
| 5,411,548 | A | 5/1995 | Carman | |
| 5,423,329 | A * | 6/1995 | Ergas | 600/546 |
| 5,452,719 | A | 9/1995 | Eisman et al. | |
| 5,562,717 | A * | 10/1996 | Tippey et al. | 607/41 |
| 5,693,000 | A * | 12/1997 | Crosby et al. | 600/16 |
| 5,807,397 | A | 9/1998 | Barreras | |
| 6,061,596 | A | 5/2000 | Richmond et al. | |
| 6,135,945 | A | 10/2000 | Sultan | |
| 6,328,687 | B1 * | 12/2001 | Karram et al. | 600/31 |
| 6,354,991 | B1 * | 3/2002 | Gross et al. | 600/29 |
| 6,652,449 | B1 * | 11/2003 | Gross et al. | 600/30 |
| 6,658,297 | B2 | 12/2003 | Loeb | |
| 6,735,474 | B1 | 5/2004 | Loeb et al. | |
| 6,862,480 | B2 * | 3/2005 | Cohen et al. | 607/41 |
| 6,896,651 | B2 * | 5/2005 | Gross et al. | 600/30 |
| 2001/0003799 | A1 | 6/2001 | Boveja | |
| 2002/0055761 | A1 | 5/2002 | Mann et al. | |
| 2003/0018365 | A1 | 1/2003 | Loeb | |
| 2003/0236557 | A1 | 12/2003 | Whitehurst et al. | |
| 2003/0236558 | A1 | 12/2003 | Whitehurst et al. | |
| 2004/0015204 | A1 | 1/2004 | Whitehurst et al. | |
| 2004/0015205 | A1 | 1/2004 | Whitehurst et al. | |
| 2004/0059392 | A1 | 3/2004 | Parramon et al. | |

OTHER PUBLICATIONS

European Search Report, EP 06011641 Aug. 10, 2006.

* cited by examiner

INCONTINENCE TREATMENT DEVICE

CROSS-REFERENCE TO RELATED APPLICATIONS

This application is a continuation of U.S. patent application Ser. No. 10/047,135 (now U.S. Pat. No. 6,896,651), filed Jan. 15, 2002, which is a continuation of U.S. patent application Ser. No. 09/413,272 (now U.S. Pat. No. 6,354, 991), filed Oct. 6, 1999, which is a continuation-in-part of U.S. patent application Ser. No. 09/167,244, now abandoned, which is incorporated herein by reference.

FIELD OF THE INVENTION

The present invention relates generally to medical electronic devices, and specifically to implantable electrical muscle stimulators.

BACKGROUND OF THE INVENTION

Urinary stress incontinence affects millions of people, causing discomfort and embarrassment, sometimes to the point of social isolation. Stress incontinence results from weakness or inability of pelvic muscles to hold back urinary flow from the bladder when abdominal pressure increases due to everyday events such as coughing, laughing or mild physical exertion. Muscles involved in controlling the urinary flow include primarily the urethral sphincter and the levator ani, with the cooperation of fibromuscular extensions along the urethra and other muscles in the general region of the pelvic diaphragm. In the United States, it is estimated that 10-13 million patients seek medical care for incontinence each year, of whom about 35% suffer from stress-type incontinence.

Stress incontinence is typically associated with either or both of the following anatomical conditions:

Urethral hypermobility—Weakness of or injury to pelvic floor muscles causes the bladder to descend during abdominal straining or pressure, allowing urine to leak out of the bladder. This is the more common source of stress incontinence.

Intrinsic sphincter deficiency—In this condition, the urethral musculature is unable to completely close the urethra or keep it closed during stress.

A large variety of products and treatment methods are available for personal and medical care of incontinence. Most patents suffering from mild to moderate incontinence use diapers or disposable absorbent pads. These products are not sufficiently absorbent to be effective in severe cases. They are uncomfortable to wear, and cause skin irritation, as well as unpleasant odors. Other non-surgical products for controlling incontinence include urethral inserts (or plugs) and externally-worn adhesive patches. Drugs are also used in some cases.

Various surgical procedures have been developed for bladder neck suspension, primarily to control urethral hypermobility by elevating the bladder neck and urethra. These procedures typically use bone anchors and sutures or slings to support the bladder neck. The success rates for bladder neck suspension surgery in controlling urinary leakage are typically in the 60-80% range, depending on the patient's condition, the surgeon and the procedure that is used. The disadvantages of surgery are its high cost, need for hospitalization and long recovery period, and high frequency of complications.

For serious cases of intrinsic sphincter deficiency, artificial urinary sphincters have been developed. For example, the AMS 800 urinary sphincter, produced by American Medical Systems Inc., of Minnetonka, Minn., includes a periurethral inflatable cuff, used to overcome urinary incontinence when the function of the natural sphincter is impaired. The cuff is coupled to a manually-operated pump and a pressure regulator chamber, which are implanted in a patient's body together with the cuff. The cuff is maintained at a constant pressure of 60-80 cm of water, which is generally higher than the bladder pressure. To urinate, the patient releases the pressure in the cuff by pressing on the implanted pump, which pumps the fluid out of the cuff to the chamber. Aspects of this system are described in U.S. Pat. No. 4,222,377, whose disclosure is incorporated herein by reference.

This artificial sphincter has several shortcomings, however. The constant concentric pressure that the peripheral cuff exerts on the urethra results in impaired blood supply to tissue in the area, leading to tissue atrophy, urethral erosion and infection. Furthermore, the constant pressure in the cuff is not always sufficient to overcome transient increases in bladder pressure that may result from straining, coughing, laughing or contraction of the detrusor muscle, for example. In such cases, urine leakage may result.

U.S. Pat. Nos. 4,571,749 and 4,731,083, whose disclosures are incorporated herein by reference, describe an artificial sphincter device whose pressure can vary in response to changes in abdominal or intravesical (bladder) pressure. The device includes a periurethral cuff with subdermal pump and pressure regulator, with the addition of a hydraulic pressure sensor. This system is complicated, however, and requires manual manipulation of the subdermal pump and cuff control.

Medtronic Neurological, of Columbia Heights, Minn., produces a device known as Interstim for treatment of urge incontinence, which is a different disorder from stress incontinence. In urge incontinence, a sudden, urgent need to pass urine causes involuntary urination, before the patient can get to a toilet. The condition may be caused by damage to nerve pathways from the brain to the bladder or by psychosomatic factors, leading to involuntary bladder contraction. Interstim uses an implantable pulse generator, which is surgically implanted in the lower abdomen and wired to nerves near the sacrum (the bone at the base of the spine) in a major surgical procedure under general anesthesia. Electrical impulses are then transmitted continuously to a sacral nerve that controls urinary voiding. The continuous electrical stimulation of the nerve has been found to reduce or eliminate urge incontinence in some patients.

Exercise and behavioral training are also effective in some cases in rehabilitating pelvic muscles and thus reducing or resolving incontinence. Patients are taught to perform Kegel exercises to strengthen their pelvic muscles, which may be combined with electrical stimulation of the pelvic floor. Electromyographic biofeedback may also be provided to give the patients an indication as to the effectiveness of their muscular exertions. Retraining muscles is not possible or fully effective for most patients, however, particularly when there may be neurological damage or other pathologies involved.

U.S. Pat. No. 3,628,538, whose disclosure is incorporated herein by reference, describes apparatus for stimulating a muscle, using an electromyogram (EMG) signal sensed in the muscle. If the signal is greater than a predetermined threshold value, a stimulator circuit applies a voltage to electrodes adjacent to the muscle. The apparatus is said to be particularly useful in overcoming incontinence.

Various types of electrodes have been proposed for applying electrical stimulation to pelvic muscles so as to prevent unwanted urine flow through the urethra. For example, U.S. Pat. No. 5,562,717 describes electrodes that are placed on the body surface, typically in the areas of the porineum and the sacrum, and are electrically actuated to control incontinence. U.S. Pat. No. 4,785,828 describes a vaginal plug having electrodes on an outer surface thereof. A pulse generator in the plug applies electrical pulses to the electrodes so as to constrict the pelvic muscles and prevent urine flow. U.S. Pat. No. 4,153,059 describes an intra-anal electrode, to which repetitive electrical pulses are applied in order to control urinary incontinence. U.S. Pat. No. 4,106,511 similarly describes an electrical stimulator in the form of a plug for insertion into the vagina or the anus. U.S. Pat. No. 3,666,613 describes a pessary ring having two electrodes thereon, which are energized to control incontinence. The disclosures of all of the above-mentioned patents are incorporated herein by reference.

U.S. Pat. No. 4,580,578, whose disclosure is also incorporated herein by reference, describes a device for stimulating the sphincter muscles controlling the bladder. A supporting body is fitted into the patient's vulva between the labia, so that two electrodes attached to the supporting body contact the epidermal surface on either side of the external urethral orifice. Electrical impulses are applied to the electrodes to stimulate the region of the sphincter.

SUMMARY OF THE INVENTION

It is an object of some aspects of the present invention to provide an improved device and method of treatment for incontinence, particularly urinary stress incontinence.

It is a further object of some aspects of the present invention to provide a device and method for enhancing function of muscles, particularly those associated with urine control.

In preferred embodiments of the present invention, an implantable device for treatment of urinary stress incontinence comprises a control unit and one or more electrodes coupled to the control unit. The electrode or electrodes are preferably implanted in the genital region of a patient so as to contact one or more of the muscles that are used in regulating urine flow from the bladder. The control unit is preferably implanted under the skin of the abdomen or genital region. Motion of or pressure on or in the area of the bladder generates an electromyographic (EMG) signal in the muscles, which is sensed by the one or more electrodes and analyzed by the control unit. Alternatively or additionally, non-electromyographic signals are received and analyzed by the control unit, as described hereinbelow. When the control unit determines that the signals are indicative of a condition, such as an increase in abdominal or intravesical pressure, that is likely to cause involuntary urine flow from the bladder, it applies an electrical waveform to the electrode or electrodes, stimulating the contacted muscle to contract and thus to inhibit the urine flow.

In some preferred embodiments of the present invention, the device also includes one or more other physiological sensors, which generate signals responsive to motion or to intravesical or abdominal pressure, or to urine volume in the bladder. These signals are thus indicative of possible incontinence that may occur due to coughing, laughing, or other strain or motion of the abdominal muscles. On the other hand, when the urine volume in the bladder is low, there will be no urine flow even when the abdominal pressure does increase. The control unit processes the signals from the other sensors and uses them to determine when the electrical stimulation should be applied to the muscles.

Preferably, the control unit comprises a processor, which is programmed to distinguish between signals indicative of possible incontinence and other signals that do not warrant stimulation of the muscles. In particular, the processor is preferably programmed to recognize signal patterns indicative of normal voiding, and does not stimulate the muscles when such patterns occur, so that the patient can pass urine normally. Preferably, the processor analyzes both long-term and short-term variations in the signals, as well as rakes and patterns of change in the signals. Most preferably, in response to the analysis, the processor: (a) makes an assessment of the patient's physiological condition, such as of the patient's bladder fill level, (b) responsive to the assessment, adjusts a time-varying threshold level associated with an aspect of the EMG signal (e.g., magnitude and/or rate) that varies over time, and (c) applies the stimulation only when a transient variation in the aspect of the EMG signal exceeds the threshold.

Further preferably, in order to reduce consumption of electrical power, the control unit comprises a low-power, low-speed processor, which monitors the EMG signals continuously, and a high-speed processor, which turns on only when the low-speed processor detects an increase in EMG activity. The high-speed processor performs an accurate analysis of the signals to determine whether stimulation is actually warranted. The inventor have found that the signals must generally be analyzed at a sample rate greater than 1000 Hz in order to accurately forecast whether or not involuntary urine loss is about to occur.

Preferably, the electrodes are implanted (unlike electrical muscle stimulators known in the art) and generally apply electrical stimulation directly into the muscle only when contraction is actually required, preferably as indicated by intrinsic physiological signals. At other times, stimulation is not applied, and the muscles are allowed to relax. Implantation of the device provides reliable, typically long-term control or muscle function, and relieves incontinence in a manner that is unobtrusive and minimizes inconvenience and discomfort of the patient. The stimulation mimics the natural function of the muscles in maintaining urinary continence. Repeated stimulation using these embodiments of the present invention also tends to exercise and strengthen the muscles, thus enhancing their inherent capability to control urine flow. Direct stimulation of the muscles, in accordance with the principles of these embodiments of the present invention, is believed to be effective against urine loss due to substantially all common types of stress incontinence.

Although preferred embodiments of the present invention are described with reference to treatment of urinary stress incontinence, it will be appreciated that the principles of the present invention may be applied as well to treat other types of urinary incontinence, such as urge incontinence, to treat fecal incontinence, and to treat and enhance the function of other muscles in the body. Alternatively or additionally, principles of the present invention may be applied to treating constipation or pathological retention of urine, typically by stimulating some muscles to contract (e.g., muscles of the colon), while stimulating some parasympathetic nerves to induce relaxation of other muscles (e.g., the muscles of the anus). These applications of the invention may be particularly useful following spinal cord injury.

There is therefore provided, in accordance with a preferred embodiment of the present invention, a device for treatment of urinary stress incontinence, including:

at least one electrode, which is implanted in a pelvic muscle of a patient; and control unit, which receives signals indicative of abdominal stress in the patient and responsive thereto applies an electrical waveform to the electrode which stimulates the muscle to contract, so as to inhibit involuntary urine flow through the patient's urethra due to the stress.

Preferably, the signals include electromyographic signals received from the at least one electrode, and the device includes a switch between the electrode and an input of the control unit, which switch is opened when the electrical waveform is applied so as to prevent feedback from the electrode to the input.

Preferably, the control unit includes a processor, which analyzes the signals so as to determined when an involuntary urine flow is likely, whereupon the waveform is applied. Further preferably, the processor distinguishes between signals indicative of an involuntary urine flow and signals indicative of voluntary voiding by the patient. Preferably, the processor is programmable to vary one or more parameters associated with the application of the waveform, and the device includes a wireless receiver, which receives data for programming the processor from a programming unit outside the patient's body.

Preferably, the processor's analysis is performed on substantially non-rectified data. Further preferably, the processor analyzes the signals using spectral analysis. Most preferably, the spectral analysis is performed by the processor on substantially non-rectified data.

Preferably, the at least one electrode includes a single unipolar electrode or, alternatively or additionally, a pair of bipolar electrodes. Further preferably, the at least one electrode includes a flexible intra-muscular electrode.

In a preferred embodiment, the device includes a physiological sensor coupled to the patient's bladder, which sensor provides at least some of the signals to the control unit. Preferably, the sensor includes a pressure sensor or, alternatively or additionally, an acceleration sensor.

Preferably, the at least one electrode and the control unit are implanted in the body of the patient, and the control unit includes a rechargeable power source. Most preferably, the power source is recharged by inductive energy transfer, substantially without electrical contact between the control unit and any object outside the patient's body.

Preferably, the pelvic muscle includes the levator ani muscle or, alternatively or additionally, the urethral sphincter muscle or another muscle adjacent to the urethral sphincter muscle.

There is further provided, in accordance with a preferred embodiment of the present invention, a device for treatment of urinary incontinence in a patient, including:

a sensor, which is coupled to generate a signal responsive to a fill level of the patient's bladder; and a control unit, which receives and analyzes the signal from the sensor so as to determine a fill level of the bladder and responsive thereto applies stimulation to a pelvic muscle of the patient, so as to inhibit involuntary flow of urine through the patient's urethra when the fill level of the bladder is above a threshold level.

Preferably, the control unit receives a further signal indicative of abdominal stress and applies the stimulation to the pelvic muscle responsive to the stress except when the fill level of the bladder is below the threshold level. In a preferred embodiment, the sensor includes an electrode, which is plated in electrical contact with the pelvic muscle of the patient to receive an electromyogram signal therefrom indicative of the stress and of the fill level.

Preferably, the device includes an electrode, which is placed in electrical contact with the pelvic muscle of the patient, and the control unit applies an electrical waveform to the electrode so as to stimulates the muscle to contract, thereby inhibiting the involuntary flow of urine.

In another preferred embodiment, the sensor includes a pressure sensor or, alternatively or additionally, an ultrasound transducer.

There is moreover provided, in accordance with a preferred embodiment of the present invention, a device for treatment of urinary stress incontinence, including:

at least one electrode, which is placed in electrical contact with a pelvic muscle of a patient; and a control unit, which receives electromyogram signals from the electrode indicative of abdominal stress in the patient, and which determines a threshold signal level that varies over time responsive to a condition of the patient, and which, responsive to a transient increase in the electromyogram signal above the threshold level, applies an electrical waveform to the electrode which simulates the muscle to contract, so as to inhibit involuntary urine flow through the patient's urethra due to the stress.

Preferably, the threshold signal level varies over time responsive to temporal variation of a mean value of the electromyogram signals. Additionally or alternatively, the threshold signal level increases responsive to time elapsed since the patient last passed urine or responsive to an increase in a fill level of the patient's bladder.

There is additionally provided, in accordance with a preferred embodiment of the present invention, a device for treatment of urinary stress incontinence, including:

at least one electrode, which is placed in electrical contact with a pelvic muscle of a patient; and a control unit, which receives electromyogram signals from the electrode and, responsive to a rate of change of the signals indicative of a possible involuntary urine flow, applies an electrical waveform to the electrode which stimulates the muscle to contract, so as to inhibit the involuntary urine flow.

Preferably, when the rate of change is below a threshold rate, the control unit withholds the waveform so as to allow voluntary voiding.

There is also provided, in accordance with a preferred embodiment of the present invention, a method for treatment of urinary stress incontinence of a patient, including:

implanting an electrode in a pelvic muscle of the patient;

receiving a signal from the patient's body indicative of abdominal stress; and responsive to the signal, applying an electrical waveform to the electrode, which stimulates the muscle to contract so as to inhibit involuntary urine flow through the urethra due to the stress.

Preferably, applying the electrical waveform includes implanting an electrode in the patient's body in electrical contact with the pelvic muscle, most preferably with the levator ani muscle or, alternatively or additionally, in contact with the urethral sphincter muscle or in proximity thereto.

Further preferably, applying the waveform includes applying a waveform to the electrode in a unipolar mode. Alternatively or additionally, implanting the electrode includes placing at least two electrodes in electrical contact with the muscle, and applying the waveform includes applying a waveform between the electrodes in a bipolar mode.

Preferably, receiving the signal includes receiving an electromyographic signal.

In a preferred embodiment, receiving the signal includes receiving a signal indicative of pressure on the patient's bladder or, alternatively or additionally, receiving a signal indicative of motion of the patient's bladder.

Preferably, applying the waveform includes analyzing the signal to determine when an involuntary urine flow is likely, and applying a waveform dependent on the determination, wherein analyzing the signal preferably includes distinguishing between a signal indicating that the involuntary urine flow is likely and another signal indicative of voluntary voiding.

Preferably, analyzing the signal includes analyzing substantially non-rectified data. Further preferably, analyzing the signal includes performing a spectral analysis. Most preferably, performing the spectral analysis includes performing the spectral analysis on substantially non-rectified data.

In a preferred embodiment, applying the waveform includes varying a parameter of the waveform selected from a group including amplitude, frequency, duration, wave shape and duty cycle. Alternatively or additionally, applying the waveform includes applying a pulse burst.

There is further provided, in accordance with a preferred embodiment of the present invention, a device for treatment of urinary stress incontinence, including:

at least one electrode, which is placed in electrical contact with a pelvic muscle of a patient; and a control unit, which receives signals indicative of impending urine flow, and distinguishes signals indicative of an involuntary urine flow from signals indicative of voluntary voiding by the patient, and responsive thereto applies an electrical waveform to the electrode which stimulates the muscle to contract, so as to inhibit involuntary urine flow.

Preferably, the control unit distinguishes between the signals indicative of an involuntary urine flow and the signals indicative of voluntary voiding, substantially without application of an input to the control unit from outside the patient's body.

There is still further provided, in accordance with a preferred embodiment of the present invention, a device for treatment of urinary stress incontinence, including:

at least one electrode, which is placed in electrical contact with a pelvic muscle of a patient; and a control unit, which receives at a sample rate substantially greater than 1000 Hz signals indicative of abdominal stress in the patient, analyzes the signals so as to determine when an involuntary urine flow is likely and responsive thereto applies an electrical waveform to the electrode which stimulates the muscle to contract, so as to inhibit involuntary urine flow through the patient's urethra due to the stress.

There is moreover provided, in accordance with a preferred embodiment of the present invention, a device for treatment of urinary stress incontinence, including:

at least one electrode, which is placed in electrical contact with a pelvic muscle of a patient;

a first processor, which receives signals indicative of abdominal stress in the patient and analyzes the signals substantially continuously at a low data analysis rate; and a second processor, which, responsive to a determination by the first processor that involuntary urine flow is likely to occur, is actuated by the first processor to analyze the signals at a high data analysis rate and; responsive to the analysis at the high data rate, applies an electrical waveform to the electrode which stimulates the muscle to contract, so as to inhibit involuntary urine flow.

There is also provided, in accordance with a preferred embodiment of the present invention, a method for treatment of urinary stress incontinence of a patient, including:

placing an electrode in electrical contact with a pelvic muscle of the patient;

receiving a signal from the patient's body indicative of abdominal stress;

analyzing the received signal to distinguish between a signal indicating that involuntary urine flow is likely and another signal indicative of voluntary voiding; and responsive to the analysis, applying an electrical waveform to the electrode, which stimulates the muscle to contract so as to inhibit involuntary urine flow.

There is further provided, in accordance with a preferred embodiment of the present invention, a method for treatment of urinary stress incontinence of a patient, including:

placing an electrode in electrical contact with a pelvic muscle of the patient;

receiving at a sample rate substantially greater than 1000 Hz signals indicative of abdominal stress;

analyzing the signals so as to determine when an involuntary urine flow is likely; and responsive to the analysis, applying an electrical waveform to the electrode, which stimulates the muscle to contract so as to inhibit involuntary urine flow.

The present invention will be more fully understood from the following detailed description of the preferred embodiments thereof, taken together with the drawings in which:

DETAILED DESCRIPTION OF PREFERRED EMBODIMENTS

Figure 1:
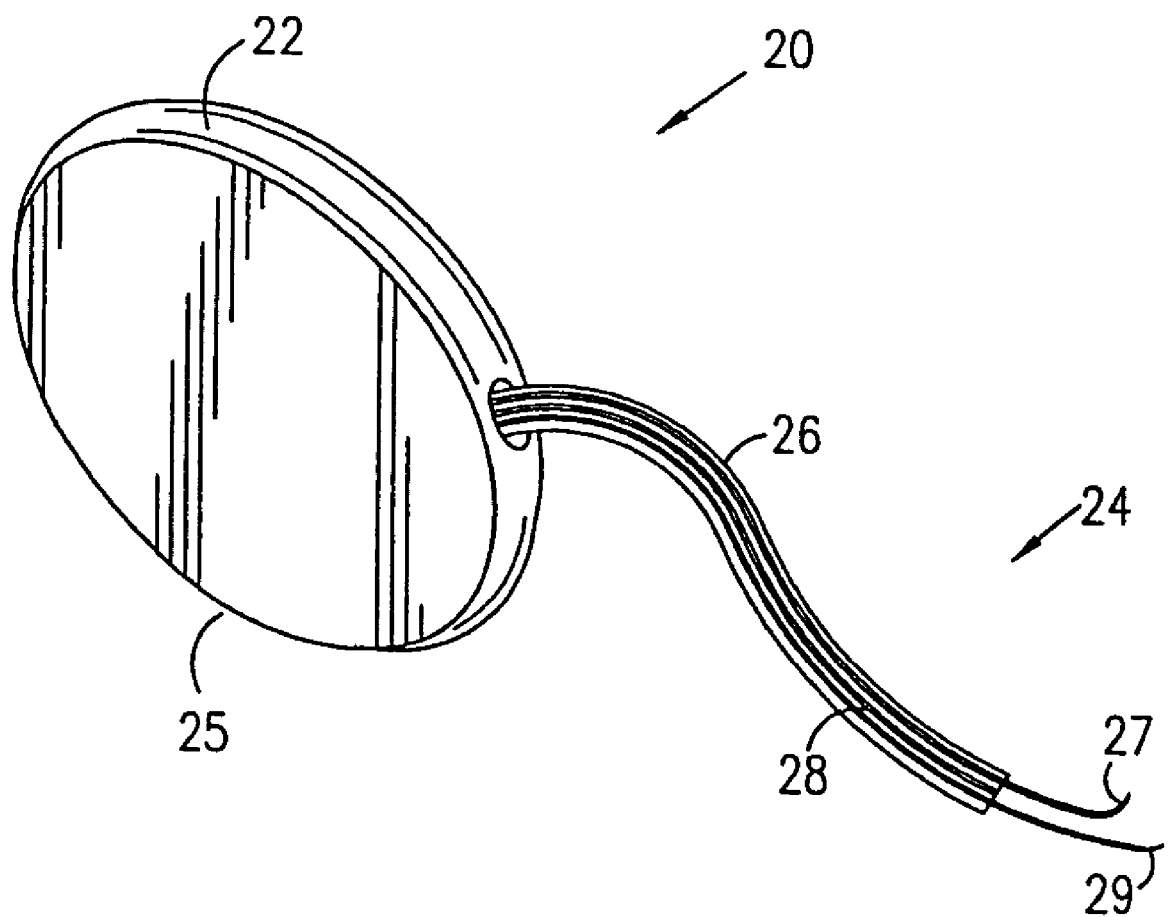
FIG. 1 is a schematic, pictorial view of an implantable muscle stimulation device, in accordance with a preferred embodiment of the present invention.

I. Overview of Preferred Embodiments
  A. General description of stimulator device
  B. Sensing and control functions of the device
  C. Signal processing
  D. Power consumption control II. Detailed Description of Figures
  A. External elements of a stimulator device
  B. Anatomical and surgical considerations
  C. Signal processing
    (i) hardware and algorithms
    (ii) simulation of a typical EMG
    (iii) experimentally measured EMG signals: distinguishing incontinence from voluntary voiding
  D. Muscle stimulation
  E. Provision of power to the control unit
  F. External communication with the control unit
  G. Utilization of other sensors
  H. Reduction of power consumption I. Overview of Preferred Embodiments
  A. General Description of Stimulator Device Various aspects of the present invention are described in this section (I) and in greater detail in the following section (II). As described with reference to the preferred embodiment shown in FIG. 1, an electronic muscle stimulator device is implanted in the genital region of a patient and stimulates one or more of the muscles in the region, so as to control and treat urinary stress incontinence. Preferably, motion of or pressure on or in the area of the patient's urinary bladder generates an electromyographic (EMG) signal in the muscles, which is sensed by one or more electrodes and is analyzed by a control unit of the device. Alternatively or additionally, non-electromyographic signals are received and analyzed by the control unit. When the control unit determines that the signals are indicative of a condition, such as an increase in abdominal or intravesical pressure, that is likely to cause involuntary urge flow from the bladder, it applies an electrical waveform to the one or more electrodes, stimulating the contacted muscle to contract and thus to inhibit the urine flow.

B. Sensing and Control Functions of the Device

In addition to EMG sensing electrodes, the device preferably also comprises one or more other physiological sensors, described hereinbelow with reference to FIGS. 2-4, which generate signals responsive to motion, to intravesical or abdominal pressure, or to urine volume in the bladder. These signals are indicative of possible incontinence that may occur due to coughing, laughing, or other strain or motion of the abdominal muscles. Typically, when the urine volume in the bladder is low, there will be no urine flow even when the abdominal pressure does increase. As described with reference to a plurality of the figures, the control unit preferably processes the signals from the other sensors and uses them to determine when the electrical stimulation should be applied to the muscles.

C. Signal Processing

Preferably, the control unit comprises a processor, e.g., as described with reference to FIGS. 3 and 4, which is programmed to distinguish between signals indicative of possible incontinence and other signals that do not warrant stimulation of the muscles. In particular, the processor is preferably programmed to recognize signal patterns indicative of normal voiding, and does not stimulate the muscles when such patterns occur, so that the patient can pass urine normally. Detection of normal voiding is described in more detail with reference to FIG. 7. Preferably, the processor analyzes both long-term and short-term variations in the signals, as well as rates, spectral patterns, and patterns of change in the signals. Most preferably, in response to the analysis, the processor sets a threshold of an aspect of the EMG signal that varies over time responsive to an assessment of the patient's physiological condition, and applies the stimulation only when a transient variation in the aspect of the EMG signal exceeds the threshold. Methods for modifying the threshold in real time are described with reference to FIG. 6. In the context of the present patent application and in the claims, a "time-varying threshold" is to be understood as comprising substantially any appropriate time-varying detection parameters that a person skilled in the art, having read the disclosure of the present patent application, would consider useful in applying the principles of the present invention. By way of illustration and not limitation, these time-varying detection parameters may include magnitude, rate, or other aspects of the EMG signal, and quantitative ultrasound, pressure, or acceleration measurements, as described herein.

D. Power Consumption Control

As described with reference to FIG. 5, the control unit preferably comprises a low-power, low-speed processor, which monitors the EMG signals continuously, and a high-speed processor, which turns on only when the low-speed processor detects an increase in EMG activity. Use of the two processors has been shown to significantly reduce consumption of electrical power. The high-speed processor performs an accurate analysis of the signals to determine whether stimulation is actually warranted.

II. Detailed Description of Figures
  A. External Elements of a Stimulator Device Reference is now made to FIG. 1, which is a schematic, pictorial illustration of an implantable electronic muscle stimulator device 20, in accordance with a preferred embodiment of the present invention. Device 20 is preferably implanted in the genital region of a patient, as described further hereinbelow, for use in stimulating one or more of the muscles in the region, so as to control and treat urinary stress incontinence.

Device 20 comprises a control unit 22 and electrodes 27 and 29, mutually coupled by an electrical lead 24. The electrodes are preferably flexible intramuscular-type wire electrodes, about 1-5 mm long and 50-100 microns in diameter, thus designed to minimize patient discomfort. They are typically formed in the shape of a spiral or hook, as is known in the art, so that they can be easily and permanently anchored in the muscle. The wire from which the electrodes are made comprises a suitable conductive material, preferably a biocompatible metal such as silver, a platinum/iridium alloy (90/10) or a nickel/chromium alloy. Lead 24 is preferably 5-10 cm long and has an insulating jacket 26 preferably comprising nylon, polyurethane, Teflon or other flexible, biocompatible insulating material. An optional additional wire 28 inside jacket 26 serves as an antenna for the purpose of wireless communications with device 20, as described further hereinbelow.

Control unit 22 contains circuitry, described further hereinbelow with references to FIGS. 3, 4 and 5, for receiving electrical signals from and applying a waveform to electrodes 27 and 29 via lead 24. The circuitry is preferably contained in a case 25, made of stainless steel or other suitable biocompatible metal, and is preferably about 20 mm in diameter and 4 mm thick. For some applications, the stainless steel case serves as a ground electrode for electrodes 27 and 29 when they are sensing or stimulating in a bipolar mode. Alternatively, the case may be made of a plastic material which is coated with a layer of biocompatible plastic, such as polymethyl methacrylate (PMMA) or silicone. Although two electrodes are shown attached to the control unit in FIG. 1, it is possible to use only a single electrode or, alternatively, additional electrodes and/or other sensors may similarly be coupled to the control unit, as described further hereinbelow.

B. Anatomical and Surgical Considerations

Figure 2:
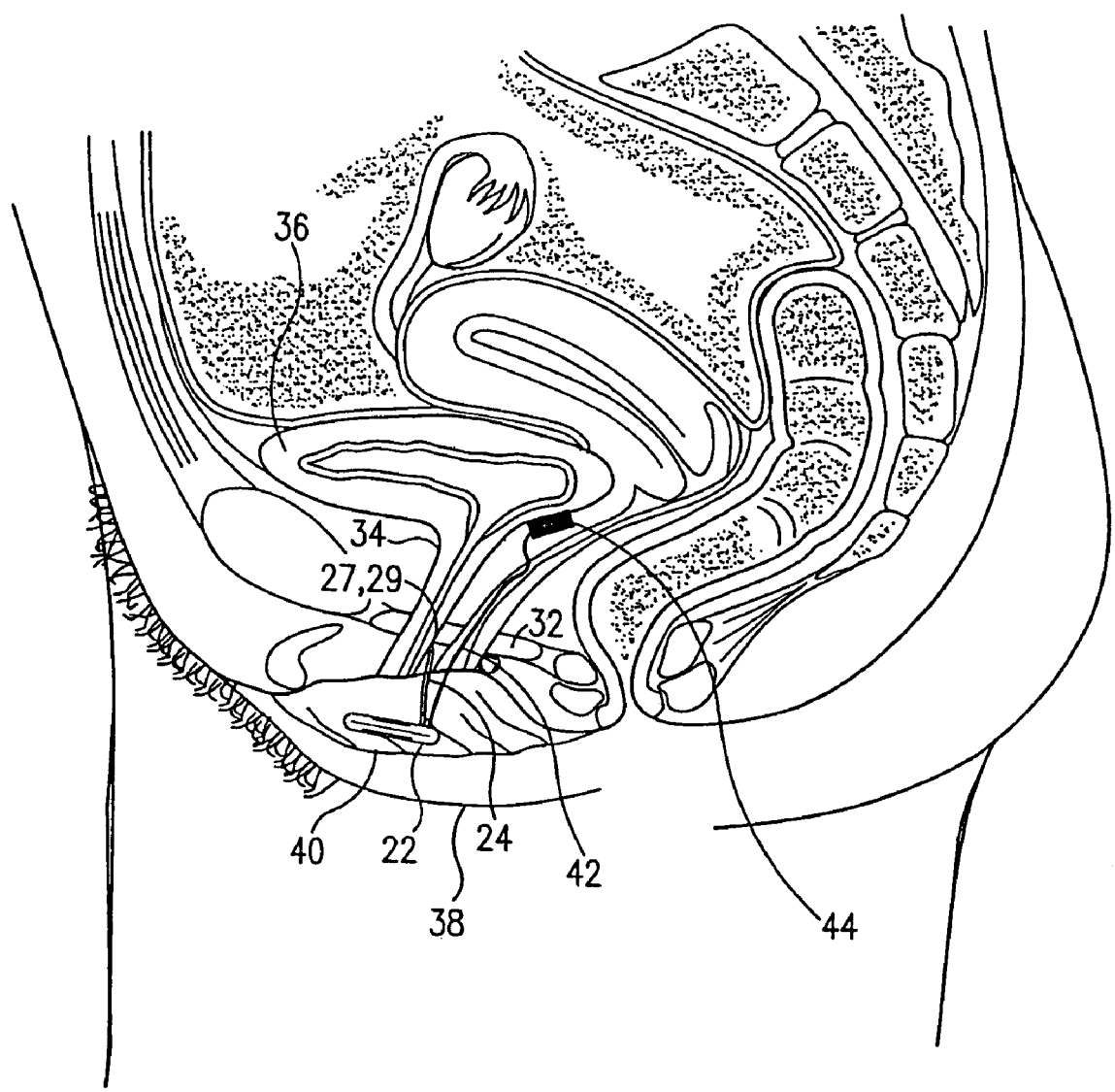
FIG. 2 is a schematic, partly sectional illustration showing implantation of the device of FIG. 1 in the pelvis of a patient, in accordance with a preferred embodiment of the present invention.

FIG. 2 is a schematic, partly sectional illustration showing the genitourinary anatomy of a female patient 31 in whom device 20 is implanted, in accordance with a preferred embodiment of the present invention. It will be appreciated that whereas preferred embodiments of the present invention are described with respect to female patients, the principles of the present invention can also be applied to male patients, mutatis mutandis. Electrodes 27 and 29 (not shown) are preferably inserted into a muscle 32, in a vicinity of urethra 34 and bladder 36. Most preferably, the electrodes are inserted into the patient's levator ani muscle, which supports and reinforces the operation of the urethral sphincter and can generally compensate for lost function of the sphincter in controlling urine flow from the bladder, such as may occur in cases of stress incontinence. The electrodes are preferably inserted through an incision made in the wall of vagina 42, and control unit 22 may likewise be implanted through this incision. Alternatively, another suitable approach may be chosen for ease of access and minimization of tissue trauma.

As noted hereinabove, the levator ani and sphincter cooperate with fibromuscular extensions along urethra 34 and with other muscles in the general vicinity of the pelvic diaphragm. Thus, one or both of the electrodes may, alternatively or additionally, be inserted into one of these other muscles, such as the puborectalis, pubococcygeus, bulboscongiosus or the urethral sphincter itself. The precise placement of the electrodes is not essential, particularly since electrical signals tend to pass among the different muscles in the region. Thus, any placement of the electrode in or on one or more of the pelvic muscles suitable for exercising urine control is considered to be within the scope of this embodiment of the present invention.

Control unit 22 is preferably implanted under the skin in the genitopelvic region of patient 31. Most preferably, the control unit is implanted inside the patient's labia minora 38 or in the labia majora 40, near muscle 32. Alternatively, the control unit is not implanted in the patient's body, but is instead maintained outside the body, connected by lead 24 to the electrodes. This configuration is convenient particularly for an initial test period, during which the effectiveness of device 20 in treating a given patient is evaluated before permanent implantation.

Optionally, a miniaturized ultrasound transducer 44 is implanted in proximity to bladder 36 and is coupled to control unit 22. Signals from the transducer are analyzed to estimate the urine volume within the bladder. When the bladder is empty, there is no need to actuate electrodes 27 and 29, even when a transient increase in the electromyogram (EMG) signal, as described hereinbelow, indicates an increase in abdominal pressure. Alternatively or additional, the EMG signal itself is analyzed to gain an indication of the urine volume in the bladder, since when the bladder is full, the average EMG activity typically increases.

C. Signal Processing

(i) Hardware and Algorithms

Figure 3:
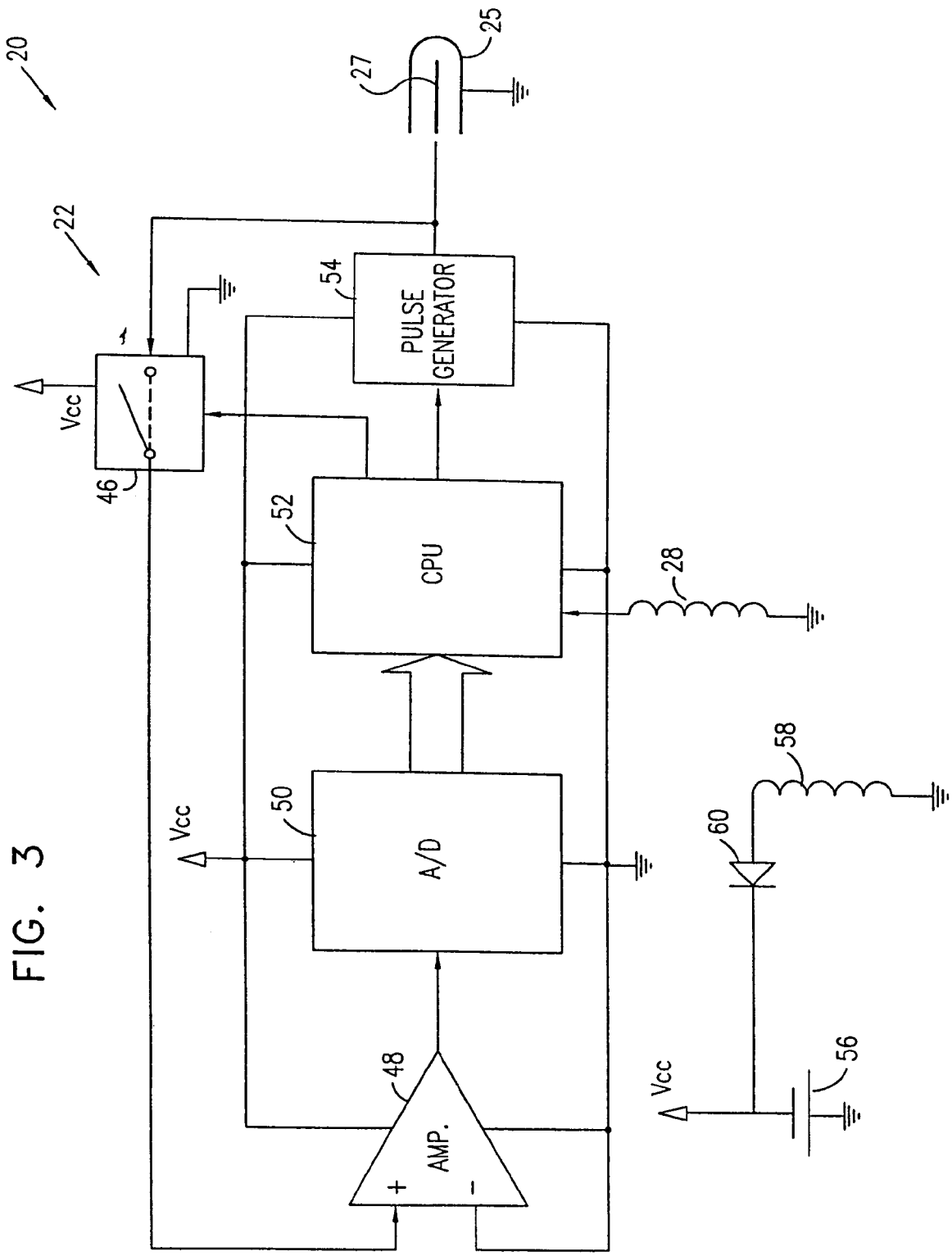
FIG. 3 is a schematic block diagram illustrating circuitry used in an implantable muscle stimulation device, in accordance with a preferred embodiment of the present invention.

FIG. 3 is a schematic block diagram showing circuitry used in control unit 22 to receive signals from and apply electrical waveforms to electrode 27, in accordance with a preferred embodiment of the present invention. Although in this embodiment, device 20 is described as operating in a unipolar mode, the principles described hereinbelow are applicable to bipolar operation, as well, in which both electrodes 27 and 29 are active.

When stress is applied to the abdomen of patient 31, electrode 27 receives EMG signals from muscle 32. These signals are conveyed via a switch 46, which is normally closed, to the input of an amplifier 48, preferably a low-noise operational amplifier. Amplified signals output from amplifier 48 are digitized by an analog/digital (A/D) converter 50 and conveyed to a central processing unit (CPU) 52, preferably a microprocessor. Preferably, although not necessarily, the amplified signals are not rectified prior to being digitized, to allow various forms of analysis, for example, spectral analysis, to be performed on the raw data, without the distortion imparted by rectification.

CPU 52 preferably analyzes these signals and/or signals from other physiological sensors, such as ultrasound, pressure, and acceleration sensors described hereinbelow, to determine whether they fit a pattern indicating that incontinence, i.e., involuntary urine flow from bladder 36, is likely to result from the stress. The pattern may correspond to coughing, laughing, or other strain or motion of the abdominal muscles. The analysis preferably comprises a spectral analysis and an analysis of EMG signal magnitude and rate. The CPU is programmed to distinguish between incontinence-related patterns and other signal patterns not associated with incontinence, such as signals generated when patient 31 wishes to pass urine voluntarily. Preferably, the CPU gathers long-term statistical information regarding the EMG and analyzes the information to "learn" common signal patterns that are characteristic of patient 31. The learned patterns are used in refining decision criteria used by the CPU in determining whether or not to apply waveforms to the electrodes.

(ii) Simulation of a Typical EMG

Figure 6:
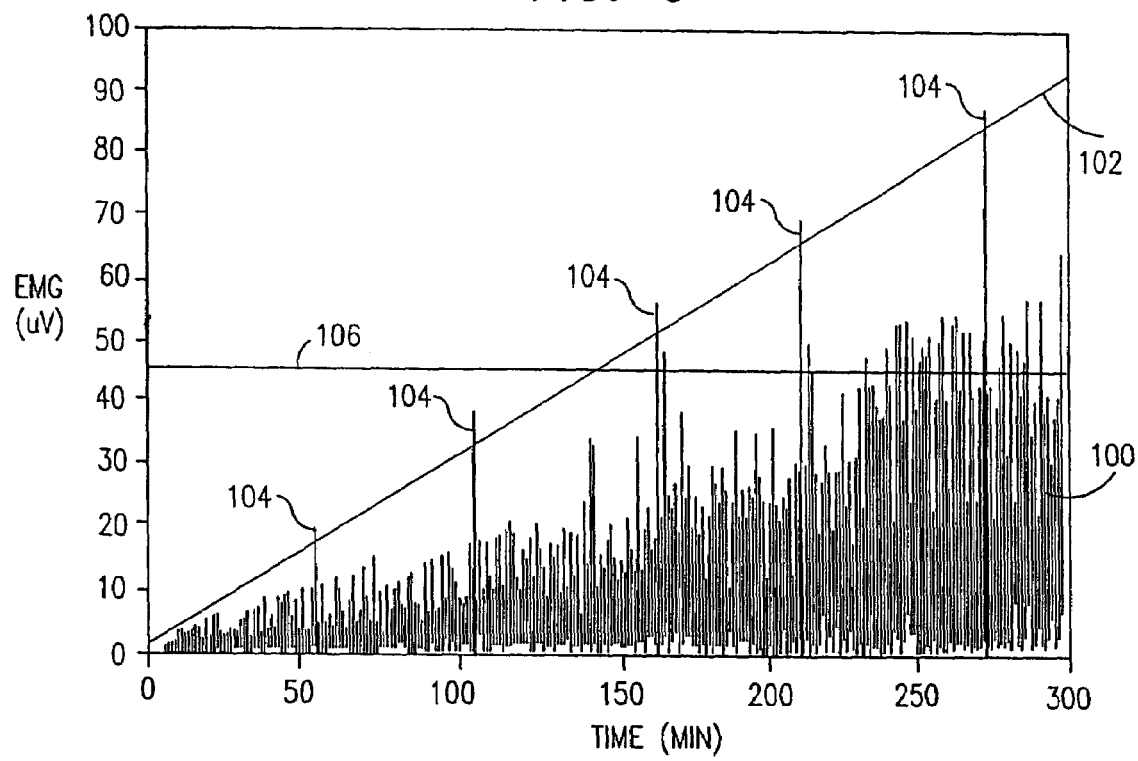
FIGS. 6 and 7 are graphs showing simulated and measured electromyogram signals, representative of different aspects of use of an implantable muscle stimulation device, in accordance with a preferred embodiment of the present invention.
Figure 7:
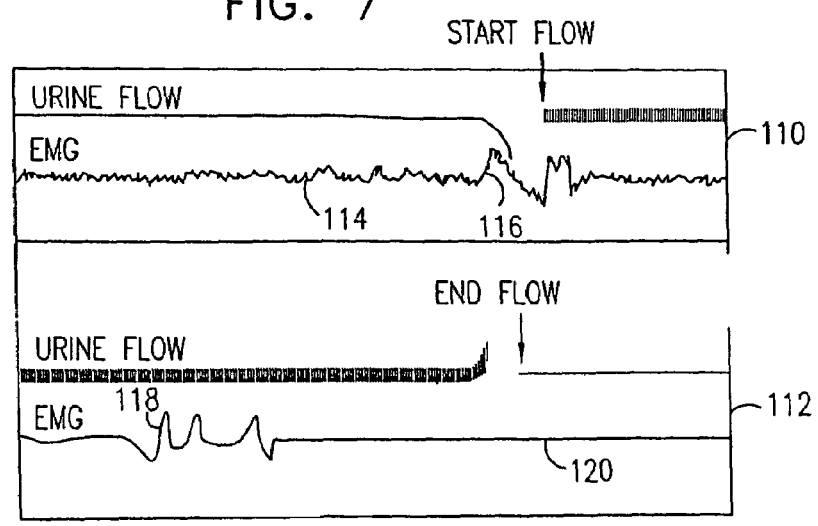

FIG. 6 is a graph that schematically illustrates results of a simulation experiment, in accordance with a preferred embodiment of the present invention, including a simulated EMG signal 100 of a woman suffering from stress incontinence. A variable, adaptive threshold level 102 as marked on the graph. Over the course of several hours, as the woman's bladder fill level increases, the average level of EMG signal 100 increases accordingly. In this example, threshold level 102 is computed so as to increase as a function of the average EMG. Alternatively or additionally, threshold level 102 and a plurality of other time-varying detection parameters are calculated as functions of other features of the EMG signal or of other aspects of the women's condition (particularly as measured by sensors 44, 76 and 78 (FIG. 4)), and are used separately or in combination in determining whether to apply stimulation to inhibit involuntary urine flow. Adaptive threshold level 102 enables five possible incidents of incontinence, marked by excursions 104 of signal 100 over level 102, to be detected reliably, with a low false alarm rate. On the other hand, if a fixed threshold level 106 is used, as is known in the art, a number of EMG excursions 104 are missed, and the false alarm rate is high.

(iii) Experimentally Measured EMG Signals: Distinguishing Incontinence from Voluntary Voiding FIG. 7 includes graphs 110 and 112 that schematically illustrate experimental measurements made before, during and after voluntary voiding of urine, in accordance with a preferred embodiment of the present invention. Graph 112 is a continuation in time of graph 110. The upper trace in both graphs illustrates urine flow, wherein the beginning and end of voluntary flow are marked by arrows. The lower trace illustrates measured EMG signals.

In a period preceding voiding, an EMG signal 114 shows substantial high-frequency activity, which is generally indicative of a full bladder. As illustrated by the graphs in the preceding figures, high-frequency spikes in signal 114 (of which none appear in FIG. 9) would be interpreted by CPU 52 as signs of imminent incontinence, leading to actuation of pulse generator 54. On the other hand, voluntary voiding is preceded by an EMG signal 116, in which there is a large but gradual increase in the signal level. Signal 116 is associated with voluntary activation of the pelvic floor muscles for the purpose of passing urine from the bladder, as is a later signal 118 during voiding. Therefore, CPU 52 analyzes not only the level of the EMG signals, but also a rate of change of the signals, in order to distinguish between voluntary and involuntary contractions of the pelvic muscles. When the rate of charge is characteristic of voluntary voiding, no stimulation is applied by pulse generator 54.

D. Muscle Stimulation

When possible incontinence is detected in this manner, CPU 52 opens switch 46 and commands a pulse generator 54 to apply a suitable electrical waveform to electrode 27 so as to stimulate muscle 32 to contract. Switch 46 is opened in order to avoid feedback of the stimulation waveform; to amplifier 48, and is closed again after the waveform is terminated. In the embodiment shown in FIG. 3, the waveform is applied to the electrode in a unipolar node, wherein case 25 of control unit 22 serves as the return (ground) electrode. (This mode can be used only when case 25 comprises a conductive material. When control unit 22 has a plastic case, at least two electrodes are generally needed, in order to administer bipolar stimulation.) As muscle 32 contracts, it closes off urethra 34, thus inhibiting the undesired urine flow. Preferably, the waveform is terminated and switch 46 is closed after a predetermined period of time, typically about 5 sec, has passed. If possible incontinence is again detected at this point, the waveform is re-applied.

It will be appreciated that, depending on the particular application, one or more waveforms may be employed in the practice of various embodiments of the present invention. For example, the waveform may be uniphasic or biphasic and may have a range of amplitudes, duty cycles and/or frequencies. It has been found generally that pulse frequencies in the range between 5 and 200 Hz are effective in engendering contraction of the levator ani and other pelvic muscles, but it may also be possible to use frequencies outside this range. In a preferred embodiment, the waveform comprises a bipolar square wave having the following characteristics:

Current 30-100 mA,
Voltage 9-15 V,
Pulse width 0.1-2.0 ms, variable in increments of 0.1 ms, and
Pulse repetition rate 30-50 Hz.

Alternatively, the waveform may comprise a decaying square wave, sinusoid or sawtooth or have any other shape found to be suitable. Further alternatively or additionally, the waveform may comprise one or more bursts of short pulses, each pulse preferably less than 1 ms in duration. Generally, appropriate waveforms and parameters thereof are determined during the initial test period.

E. Provision of Power to the Control Unit

Power is supplied to the elements of control unit 22 by a battery 56, which may comprise a primary battery (non-rechargeable) and/or a rechargeable battery. Alternatively, a super-capacitor, as is known in the art, may be used to store and provide the electrical power. If a rechargeable battery or super-capacitor is used, it is preferably recharged via an inductive coil 58 or antenna, which receives energy by magnetic induction from an external magnetic field charging source (not shown) hold in proximity to the pelvis of patient 31. The magnetic field causes a current to flow in coil 58, which is rectified by a rectifier 60 and furnished to charge battery 56. Wire 28 may also be used for this purpose.

Preferably, battery 56 comprises a standard battery, such as a lithium battery, having a nominal output of 3 volts. Most preferably, pulse generator 54 comprises a DC/DC converter, as is known in the art, and a capacitor, which is charged by the DC/DC converter to a constant, stepped-up voltage level regardless of the precise battery voltage, which may vary between 3.5 and 1.8 volts. The same DC/DC converter, or another similar device, preferably supplies power to other circuit components of control unit 22.

F. External Communication with the Control Unit

An inductive arrangement, using wire 28 coupled to CPU 52, is preferably used to program the CPU, using an external programming device (not shown) with a suitable antenna. Alternatively, the programming device generates a modulated magnetic field to communicate with a receiver inside case 25, which preferably senses the field using a Hall effect transducer. Such programming may be used, for example, to set an amplitude or duration of the stimulation waveform applied by pulse generator 54, or to set a threshold level or other parameters, according to which the CPU distinguishes between electromyographic or other signals that are indicative of impending incontinence and those that are not (e.g., those that indicate voluntary voiding). Such programming may be carried out by medical personnel or by the patient herself, who can similarly turn the implanted control unit on and off as desired by passing a suitable magnet over the area of her pelvis.

Although the circuit blocks in control unit 22 are shown as discrete elements, some or all of these blocks are preferably embodied in a custom or semi-custom integrated circuit device, as is known in the art.

G. Utilization of Other Sensors

Figure 4:
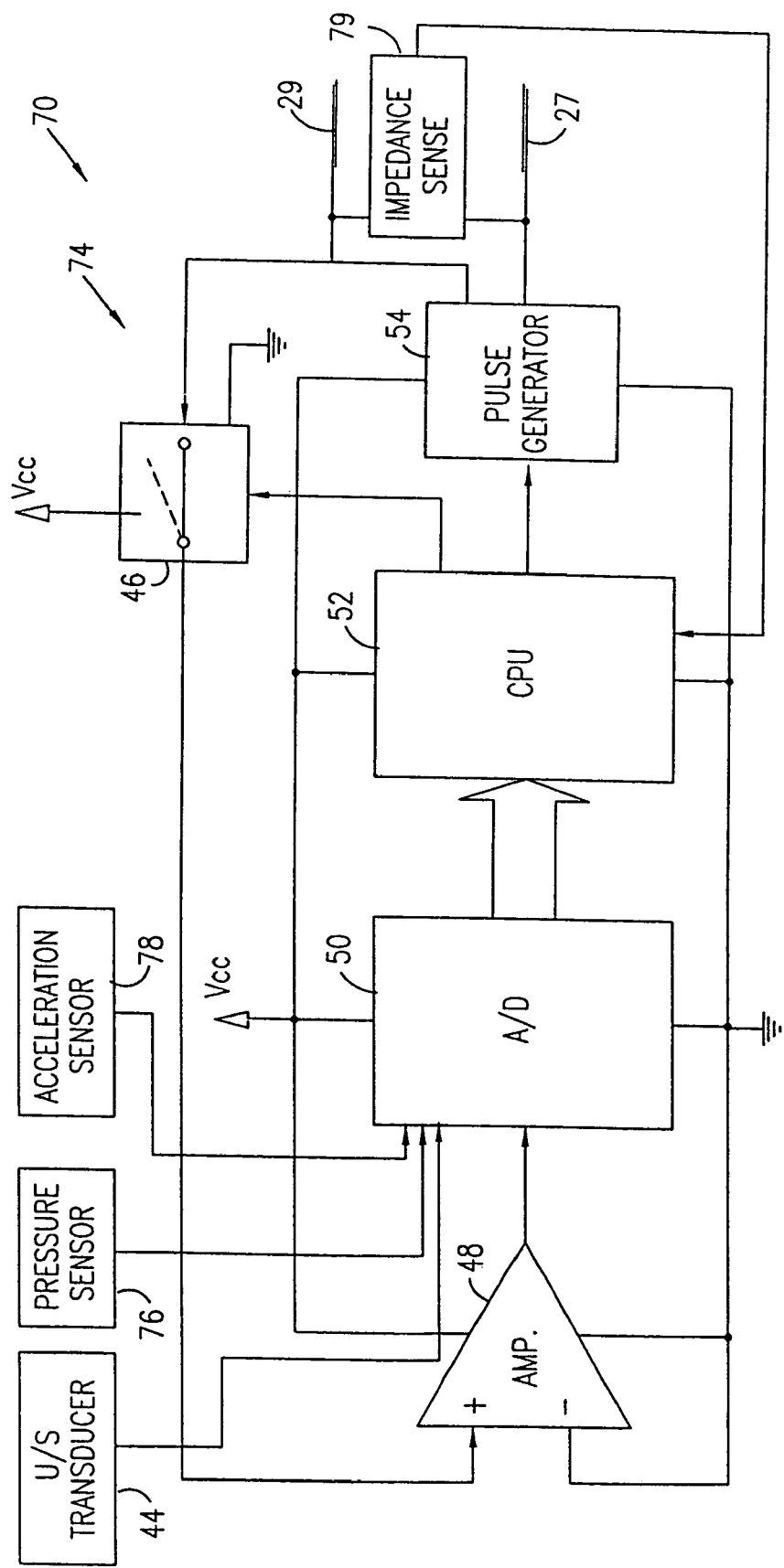
FIG. 4 is a schematic block diagram illustrating circuitry used in an implantable muscle stimulation device, in accordance with another preferred embodiment of the present invention.

FIG. 4 is a schematic block diagram illustrating a muscle stimulator device 70, in accordance with an alternative embodiment of the present invention. Device 70 is substantially similar to device 20, except for features described hereinbelow. Device 70 comprises a control unit 74, which is coupled to electrodes 27 and 29. Electrode 29 also serves as the sensing electrode, furnishing electromyographic signals via switch 46 to amplifier 48, as described hereinabove. Alternatively, electrodes 27 and 29 may be coupled as differential inputs to amplifier 48. Pulse generator 54 applies the stimulation waveforms between electrodes 27 and 29 in a bipolar mode.

In addition to or instead of the electromyographic signals received from electrode 29, CPU 52 preferably receives additional signals from other physiological sensors, such as ultrasound transducer 44 (shown in FIG. 2), a pressure sensor 76 and/or an acceleration sensor 78, or other types of strain and motion measurement devices, as are known in the art. Pressure sensor 76 is preferably implanted on or in bladder 36, so as to detect increases in abdominal or intravesical pressure that may lead to involuntary urine loss. Similarly, acceleration sensor 78 is preferably implanted so as to detect bladder motion associated with hypermobility, which is similarly associated with urine loss. The additional signals from these sensors are preferably analyzed by the CPU together with the electromyographic signals in order to improve the accuracy and reliability of detection of impending stress incontinence.

An impedance sensor 79 is used to measure the tissue impedance between leads 27 and 29, using physiological impedance measurement techniques known in the art. During long-term use of device 70 (or other such devices), fibrosis in the area of the implanted electrodes tends to cause the impedance to increase, so that the stimulating current for a given applied voltage decreases. The impedance measured by sensor 79 is used as a feedback signal instructing CPU 52 to increase the voltage, so that a generally constant level of simulation current is maintained.

H. Reduction of Power Consumption

Figure 5:
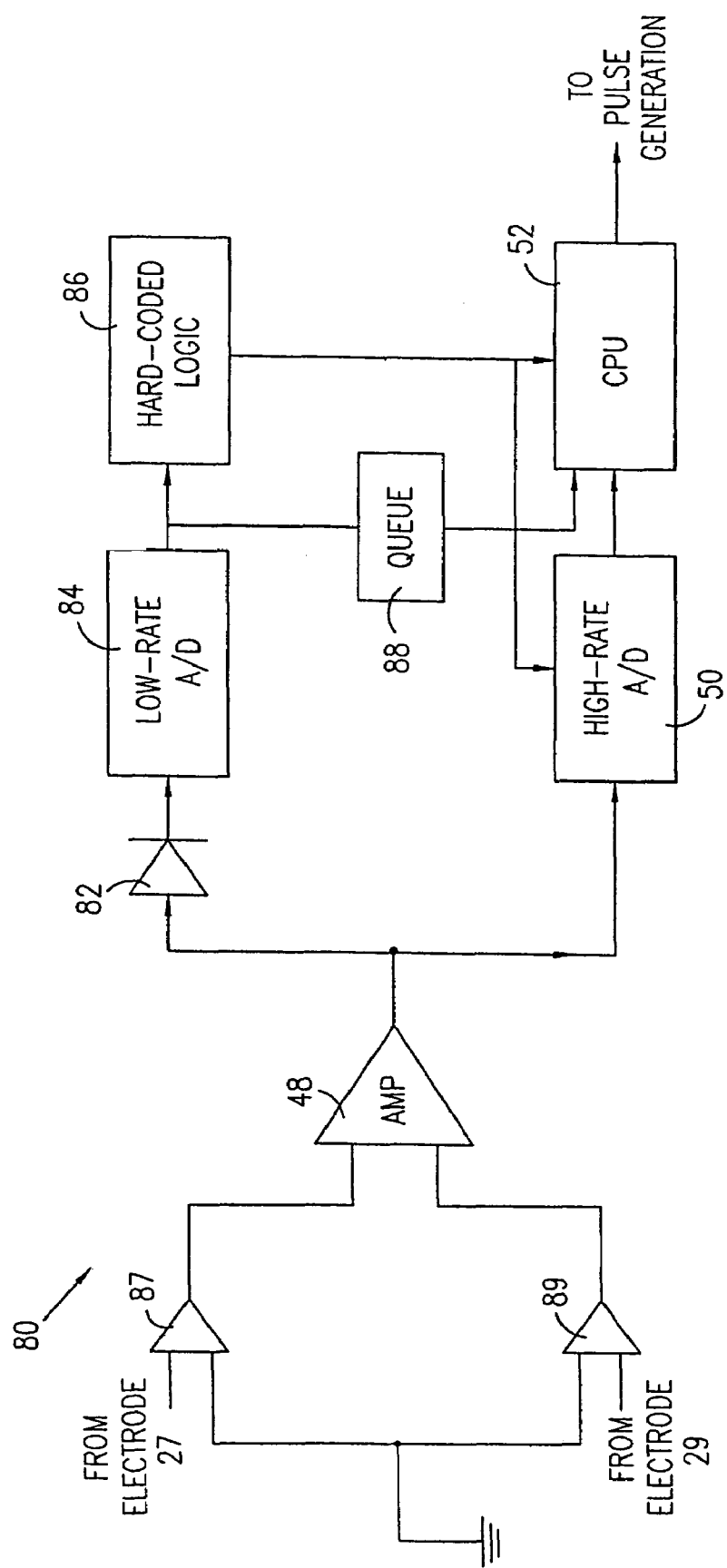
FIG. 5 is a schematic block diagram illustrating signal processing circuitry for analyzing electromyogram signals, in accordance with a preferred embodiment of the present invention.

FIG. 5 is a schematic block diagram showing details of signal processing circuitry 80 for use in device 20 or 70, in accordance with a preferred embodiment of the present invention. In order to detect impending incontinence with adequate reliability, A/D converter 50 must typically sample the EMG signals from the electrodes at 1000-5000 Hz, and CPU 52 must perform a detailed analysis of the sample stream. Systems for incontinence control known in the art, operating at sample rates below 1000 Hz, cannot adequately distinguish between signals that may be indicative of incontinence and those that are not. For the purpose of such high-rate sampling, CPU 52 preferably comprises a low-power, software-programmable processor. If A/D converter 50 and CPU 52 were to operate continuously, however, battery 56 would rapidly run down. Therefore, circuitry 80 comprises a low-power, low-resolution A/D converter 84 and hard-coded processing logic 86, which operate continuously at a low sampling rate, preferably at about 100-200 Hz. Input from amplifier 48 to A/D converter 84 is preferably rectified by a rectifier 82.

In operation, A/D converter 50 and CPU 52 are normally maintained in a standby state, in which their power consumption is negligible. When logic 86, operating at the low sampling rate, detects EMO signals that may be a precursor to incontinence, it signals A/D converter 50 to begin sampling at the high rate. In order not to lose significant data from the brief period before A/D converter 50 and CPU 52 turn on, signals from A/D converter 84 are preferably stored in a cyclic (or first-in first-out) queue 88, such as a delay line. The entire sequence of signal detection and processing is estimated to take between 5 and 20 ms, up to the point at which CPU 52 reaches a decision as to whether or not to actuate pulse generator 54. Pulse generation takes between 1 and 20 ms, with the result that contraction of the pelvic muscles begins within 15-50 ms of the onset of increased EMG activity indicating impending urine loss. Thus, urethra 34 is substantially closed off before any significant amount of mine can leak out.

As shown in FIG. 5, EMG inputs from electrodes 27 and 29 are preferably amplified before processing in a dual-differential configuration. Electrode 27 and 29 are coupled to respective differential preamplifiers 87 and 89. The outputs of the preamplifiers are differentially amplified by amplifier 48. This configuration, which affords enhanced sensitivity and reduced noise in device 70, is shown in FIG. 4.

Although preferred embodiments of the present invention are described hereinabove with reference to treatment of urinary stress incontinence, it will be appreciated that the principles of the present invention may be applied as well to treat other types of incontinence, such as urge incontinence, and to treat and enhance the function of other muscles in the body. It will be understood that the preferred embodiments described above are cited by way of example, and the full scope of the invention is limited only by the claims.

The invention claimed is:

1. An apparatus comprising:
   at least one elongated electrode structure comprising at least one electrode, the elongated electrode structure being adapted to sense an electromyographic signal indicative of urinary incontinence from a pelvic muscle of a patient; and
   a control unit coupled to the at least one electrode and comprising an electrical waveform output that is adapted to be applied to the pelvic muscle through the at least one electrode, the control unit comprising a processor that analyzes the electromyographic signal and that controls the electrical waveform output as a function of the electromyographic signal to control the urinary incontinence; and
   wherein the at least one electrode comprises a flexible intra-muscular electrode.

2. The apparatus according to claim 1, wherein the at least one elongated electrode structure is adapted to be implanted in the pelvic muscle.

3. The apparatus according to claim 1, wherein the at least one elongated electrode structure is adapted to be implanted in contact with a levator ani muscle portion of the pelvic muscle.

4. The apparatus according to claim 1, wherein the at least one elongated electrode structure is adapted to be implanted in contact with an urethral sphincter muscle portion of the pelvic muscle.

5. The apparatus according to claim 1, wherein the at least one elongated electrode structure is adapted to be implanted in contact with a portion of the pelvic muscle that is adjacent to an urethral sphincter muscle.

6. The apparatus according to claim 1, wherein the at least one elongated electrode structure is adapted to be implanted in a levator ani muscle portion of the pelvic muscle.

7. The apparatus according to claim 1, wherein the at least one elongated electrode structure is adapted to be implanted in an urethral sphincter muscle portion of the pelvic muscle.

8. The apparatus according to claim 1, wherein the at least one elongated electrode structure is adapted to be implanted in the a portion of the pelvic muscle that is adjacent to a urethral sphincter muscle.

9. The apparatus according to claim 1, wherein the electrical waveform output comprises a plurality of electrical pulses having pulse width durations in a range of 0.1 ms to 2 ms.

10. The apparatus according to claim 1, wherein the at least one electrode comprises a single unipolar electrode.

11. The apparatus according to claim 1, wherein the at least one electrode comprises a pair of bipolar electrodes.

12. The apparatus according to claim 1, wherein the electrical waveform output comprises a biphasic electrical waveform.

13. The apparatus according to claim 1, wherein the control unit controls the electrical waveform output to treat urinary incontinence of the patient.

14. The apparatus according to claim 1, wherein the control unit controls the electrical waveform output to treat urinary urge incontinence.

15. The apparatus according to claim 1, wherein the control unit controls the electrical waveform output to treat urinary stress incontinence.

16. The apparatus according to claim 1, wherein the control unit comprises a pulse generator that actuates the electrical waveform output to terminate after a predetermined period of time.

17. The apparatus according to claim 16, wherein the pulse generator actuates the pulse generator to terminate after 5 seconds.

18. The apparatus according to claim 16, wherein the control unit controls the pulse generator to reapply the electrical waveform output to the muscle through the at least one electrode after termination of the application of the electrical waveform output.

19. The apparatus according to claim 1 wherein the control unit comprises a switch that is connected to the electrode and controlled by the control unit, and the switch disconnects the analyzing of the electromyographic signal when the electrical waveform output is provided.

20. The apparatus according to claim 1 wherein the control unit comprises an impedance sensor coupled to the electrode, and the impedance sensor measures tissue impedance.

21. The apparatus according to claim 1 wherein the control unit comprises a differential preamplifier with a preamplifier input that is coupled to the electrode and a preamplifier output; and wherein the control unit further comprises an amplifier with an amplifier input that receives the preamplifier output.

22. The apparatus according to claim 1 wherein the control unit comprises a lower power A/D converter that analyzes continuously at a lower sampling rate, and a higher power A/D converter that analyzes at a higher rate when the electromyographic signal is sensed.

23. The apparatus according to claim 22 wherein the control unit comprises a first-in first-out queue that receives an A/D output of the lower power A/D converter.

24. An apparatus comprising:
at least one elongated electrode structure comprising at least one electrode, the elongated electrode structure being adapted to sense an electromyographic signal indicative of urinary incontinence from a pelvic muscle of a patient; and
a control unit coupled to the at least one electrode and comprising an electrical waveform output that is adapted to be applied to the muscle through the at least one electrode, the control unit comprising a processor that analyzes the electromyographic signal and that controls the electrical waveform output as a function of the electromyographic signal to control the urinary incontinence; and
wherein the control unit controls the pulse width duration of the waveform to a range of pulse width durations that includes 2 ms.

25. The apparatus according to claim 24 wherein the control unit comprises a switch that is connected to the electrode and controlled by the control unit, and the switch disconnects the analyzing of the electromyographic signal when the electrical waveform output is provided.

26. The apparatus according to claim 24 wherein the control unit comprises an impedance sensor coupled to the electrode, and the impedance sensor measures tissue impedance.

27. The apparatus according to claim 24 wherein the control unit comprises a differential preamplifier with a preamplifier input that is coupled to the electrode and a preamplifier output; and wherein the control unit further comprises an amplifier with an amplifier input that receives the preamplifier output.

28. The apparatus according to claim 24 wherein the control unit comprises a lower power A/D converter that analyzes continuously at a lower sampling rate, and a higher power A/D converter that analyzes at a higher rate when the electromyographic signal is sensed.

29. The apparatus according to claim 28 wherein the control unit comprises a first-in first-out queue that receives an A/D output of the lower power A/D converter.

30. An apparatus comprising:
at least one elongated electrode structure comprising at least one electrode, the elongated electrode structure being adapted to sense an electromyographic signal indicative of urinary incontinence from a pelvic muscle of a patient; and
a control unit implanted in the patient and coupled to the at least one electrode structure and comprising an electrical waveform output comprising a plurality of electrical pulses that is applied to the pelvic muscle though the electrode structure the control unit comprising a processor that analyzes the electromyographic signal and that controls the electrical waveform output as a function of the electromyographic signal to control the urinary incontinence;
wherein the control unit includes a variable adaptive threshold level that increases as a function of an average of the electromyographic signal.

31. The apparatus according to claim 30 wherein the control unit comprises a switch that is connected to the electrode and controlled by the control unit, and the switch disconnects the analyzing of the electromyographic signal when the electrical waveform output is provided.

32. The apparatus according to claim 30 wherein the control unit comprises an impedance sensor coupled to the electrode, and the impedance sensor measures tissue impedance.

33. The apparatus according to claim 30 wherein the control unit comprises a differential preamplifier with a preamplifier input that is coupled to the electrode and a preamplifier output; and wherein the control unit further comprises an amplifier with an amplifier input that receives the preamplifier output.

34. The apparatus according to claim 30 wherein the control unit comprises a lower power A/D converter that analyzes continuously at a lower sampling rate, and a higher power A/D converter that analyzes at a higher rate when the electromyographic signal is sensed.

35. The apparatus according to claim 34 wherein the control unit comprises a first-in first-out queue that receives an A/D output of the lower power A/D converter.

* * * * *

UNITED STATES PATENT AND TRADEMARK OFFICE
CERTIFICATE OF CORRECTION

PATENT NO. : 7,387,603 B2  Page 1 of 1
APPLICATION NO. : 10/999824
DATED : June 17, 2008
INVENTOR(S) : Yossi Gross et al.

It is certified that error appears in the above-identified patent and that said Letters Patent is hereby corrected as shown below:

Title Pg, Item (75) Inventors:
Change David Lifschitz, Zurich "(IL)" to David Lifschitz, Zurich --(CH)--.

Signed and Sealed this

Seventh Day of April, 2009

JOHN DOLL
*Acting Director of the United States Patent and Trademark Office*